United States Patent
Yi et al.

(10) Patent No.: US 11,690,797 B2
(45) Date of Patent: Jul. 4, 2023

(54) COSMETIC COMPOSITION COMPRISING ROSE STEM CELL-DERIVED EXOSOME AS EFFECTIVE INGREDIENT

(71) Applicant: ExoCoBio Inc., Seoul (KR)

(72) Inventors: Yong Weon Yi, Seoul (KR); Byong Seung Cho, Gunpo-si (KR)

(73) Assignee: ExoCoBio Inc., Seoul (KR)

( * ) Notice: Subject to any disclaimer, the term of this patent is extended or adjusted under 35 U.S.C. 154(b) by 271 days.

(21) Appl. No.: 17/141,693

(22) Filed: Jan. 5, 2021

(65) Prior Publication Data

US 2021/0121393 A1 Apr. 29, 2021

Related U.S. Application Data

(63) Continuation of application No. PCT/KR2019/009053, filed on Jul. 23, 2019.

(30) Foreign Application Priority Data

Jul. 26, 2018 (KR) .................. 10-2018-0087232
Jan. 30, 2019 (KR) .................. 10-2019-0011567

(51) Int. Cl.
*A61K 8/9789* (2017.01)
*A61K 8/02* (2006.01)
*A61K 8/04* (2006.01)
*A61K 8/06* (2006.01)
*A61Q 19/08* (2006.01)

(52) U.S. Cl.
CPC .......... *A61K 8/9789* (2017.08); *A61K 8/0208* (2013.01); *A61K 8/0212* (2013.01); *A61K 8/0241* (2013.01); *A61K 8/042* (2013.01); *A61K 8/044* (2013.01); *A61K 8/046* (2013.01); *A61K 8/06* (2013.01); *A61Q 19/08* (2013.01)

(58) Field of Classification Search
CPC ........ A61Q 19/08; A61Q 19/00; A61Q 19/02; A61K 8/97; A61K 2800/59; A61K 8/06; A61K 8/19; A61K 8/345; A61K 8/365; A61K 8/44; A61K 8/4946; A61K 8/498; A61K 8/64; A61K 8/73; A61K 8/735; A61K 8/9789; A61K 8/987; A61K 8/988; A61K 2800/10; A61K 31/728; A61K 8/0208; A61K 8/0212; A61K 8/0241; A61K 8/042; A61K 8/044; A61K 8/046; A61K 8/14; A61K 8/60; A61K 8/922; A61K 8/99; A61K 36/738; A61K 9/00; A61K 9/0017; A61P 29/00; A61P 17/02
See application file for complete search history.

(56) References Cited

U.S. PATENT DOCUMENTS

| | | | | |
|---|---|---|---|---|
| 2017/0152484 A1 | * | 6/2017 | Cho | ........................ A61K 35/35 |
| 2017/0209365 A1 | | 7/2017 | Cho et al. | |
| 2019/0133922 A1 | | 5/2019 | Kang et al. | |

FOREIGN PATENT DOCUMENTS

| | | | | | |
|---|---|---|---|---|---|
| CN | 104922051 A | * | 9/2015 | ............... | A61K 8/99 |
| CN | 105919886 A | | 9/2016 | | |
| CN | 107496346 | * | 12/2017 | ............... | A61K 8/60 |
| EP | 3354257 A1 | | 8/2018 | | |
| KR | 10-1519210 B1 | | 5/2015 | | |
| KR | 10-2017-0037380 A | | 4/2017 | | |
| KR | 20170037380 | * | 4/2017 | ............... | A61K 8/97 |
| KR | 10-1734994 B1 | | 5/2017 | | |
| WO | 2012/169664 A1 | | 12/2012 | | |
| WO | WO2016/057513 A1 | * | 4/2016 | ............. | A61K 36/00 |
| WO | 2017/164517 A1 | | 9/2017 | | |
| WO | 2019/088656 A1 | | 5/2019 | | |

OTHER PUBLICATIONS

KR20170037380 translation (Year: 2017).*
CN107496346 translation (Year: 2017).*
CN104922051A translation (Year: 2015).*
Plant stem cell (callus), Naver Blog. Talk on Cosmetic Ingredients, Aug. 2016, 4 pages.
International Preliminary Examining Authority, PCT/IPEA/409 in Korean for PCT/KR2019/009053 dated Nov. 23, 2020 (last visited Oct. 14, 2019).
International Searching Authority, International search report for PCT/KR2019/009053 dated Oct. 25, 2019.
International Searching Authority, Written opinion for PCT/KR2019/009053 dated Oct. 25, 2019.
Bio-FD&C Rosa Damascena Callus Culture Extract, BIO-FD&C at www.cosmo-biocom/bbs/board.php7bo_table=cosmetio_4&wr_id=2 (last visited Oct. 14, 2019).

* cited by examiner

*Primary Examiner* — Audrea B Coniglio
(74) *Attorney, Agent, or Firm* — Sughrue Mion, PLLC

(57) ABSTRACT

A cosmetic composition containing rose stem cell-derived exosomes as an active ingredient is provided for skin regeneration, skin elasticity improvement or skin wrinkle reduction. The cosmetic composition has excellent effects on skin regeneration, skin elasticity improvement and/or skin wrinkle reduction.

16 Claims, 7 Drawing Sheets
(1 of 7 Drawing Sheet(s) Filed in Color)

COSMETIC COMPOSITION COMPRISING ROSE STEM CELL-DERIVED EXOSOME AS EFFECTIVE INGREDIENT

CROSS REFERENCE

This application is a Bypass Continuation of International Application No. PCT/KR2019/009053 filed Jul. 23, 2019, claiming priority based on Korean Patent Application No. 10-2018-0087232 filed Jul. 26, 2018 and Korean Patent Application No. 10-2019-0011567 filed Jan. 30, 2019, the entire contents of which are incorporated herein by reference.

TECHNICAL FIELD

The present invention relates to a cosmetic composition for skin regeneration, skin elasticity improvement and skin wrinkle reduction containing rose stem cell-derived exosomes as an active ingredient.

BACKGROUND ART

It is known that skin aging leads to a decrease in skin elasticity and an increase in skin wrinkles and that the decrease in skin elasticity and the formation of skin wrinkles occur due to decreased synthesis of collagen and stimulated expression of the collagenase matrix metalloproteinase (MMP).

In addition, it is known that in skin cells, COX-2, an enzyme that produces inflammatory cytokines increases due to aging progression or ultraviolet (UV) rays, resulting in increased synthesis of prostaglandin E2 and increased production of inflammation inducers. Due to inflammatory reactions, the biosynthesis of MMP increases, causing collagen degradation and resulting in the decrease in skin elasticity and the formation of skin wrinkles. In particular, when sunlight and ultraviolet rays are irradiated directly onto skin, a lot of free radicals are generated, and these free radicals could damage the antioxidant defense system of skin, thus increasing wrinkles, making skin loose and accelerating skin aging. Therefore, in order to reduce skin wrinkles and maintain elasticity, it is necessary to protect skin by inhibiting the production of reactive oxygen species and free radicals, inhibiting inflammatory responses and encouraging skin regeneration from wounds.

Substances known to be effective in reducing skin wrinkles include adenosine and retinoic acid. However, adenosine has little efficacy in clinical practice, and retinoic acid cannot be used for pregnant women and has side effects such as erythema. Accordingly, functional cosmetics for anti-aging skin containing active ingredients derived from plants or natural products have recently attracted attention. However, functional cosmetics containing plant extracts as an active ingredient have problems that they may cause a foreign body sensation during their evaporation after application to the skin, and the duration of the effect thereof is short.

Recently, there have been reports that cell secretomes contain various bioactive molecules that regulate cellular behaviors. In particular, cell secretomes contain 'exosome' that has intercellular signaling functions, and thus studies on the components and functions thereof have been actively conducted.

Cells release various membraneous vesicles to their extracellular environment, and these released vesicles are usually called extracellular vesicles (EVs). The EV is also called cell membrane-derived vesicle, ectosome, shedding vesicle, microparticle, exosome, etc., and is also used discriminately from exosome in some cases.

Exosome is a vesicle of tens to hundreds of nanometers in size, which consists of a phospholipid bilayer membrane having the same structure as that of the cell membrane. This exosome contains proteins, nucleic acids (mRNA, miRNA, etc.) and the like which are called exosome cargo. It is known that exosome cargo includes a wide range of signaling factors, and these signaling factors are specific for cell types and regulated differently depending on secretory cells' environment. It is known that exosome is an intercellular signaling mediator secreted by cells, and various cellular signals transmitted through it regulate cellular behaviors, including the activation, growth, migration, differentiation, dedifferentiation, apoptosis, and necrosis of target cells. Exosome contains specific genetic materials and bioactive factors depending on the nature and state of cells from which the exosome was derived. Exosome derived from proliferating stem cells regulates cell behaviors such as cell migration, proliferation and differentiation, and recapitulates the function of stem cells involved in tissue regeneration (Nature Review Immunology 2002 (2) 569-579).

Exosomes called "avatars" of cells are known to be released not only from stem cells and cancer cells, but also from cells of various organisms such as plants, bacteria, fungi, and algae. For example, exosomes may be isolated from conditioned media of plant stem cells, as well as conditioned media of mesenchymal stem cells and conditioned media of fibroblasts.

However, studies on the isolation, purification, and characterization of exosomes derived from plant stem cells remain insufficient. Therefore, more detailed characterization and functional studies of exosomes derived from plant stem cells are required.

Various varieties of roses are cultivated in a wide range of areas such as the cold, subarctic, temperate, and subtropical zones of the northern hemisphere, and extract thereof are used in perfumes and cosmetics. However, technologies to date are at a level where extracts obtained by drying rose petals and subjecting the dried petals to hot-water extraction or solvent extraction are used for perfumes and air fresheners. In addition, conditioned media of rose callus contain growth regulators or a callus inducing substance, and thus are hardly regarded as natural cosmetic ingredients, and the growth regulators contained in the cultures may cause side effects such as skin troubles.

The present inventors have found that exosomes derived from rose stem cells are effective in skin regeneration, skin elasticity improvement and/or skin wrinkle reduction, etc., and have developed a cosmetic composition for skin regeneration, skin elasticity improvement or skin wrinkle reduction containing rose stem cell-derived exosomes as an active ingredient.

Meanwhile, it is to be understood that the matters described as the background art are intended merely to aid in the understanding of the background of the present invention and are not admitted as prior art against the present invention.

SUMMARY OF INVENTION

An object of the present invention is to provide a cosmetic composition for skin regeneration, skin elasticity improvement or skin wrinkle reduction containing rose stem cell-derived exosomes as an active ingredient.

However, the objects of the present invention as described above are illustrative and the scope of the present invention is not limited thereby. In addition, other objects and advantages of the present invention will be more apparent from the following description, the appended claims and the accompanying drawings.

DETAILED DESCRIPTION OF INVENTION

The present invention provides a cosmetic composition for skin regeneration, skin elasticity improvement or skin wrinkle reduction containing exosomes derived from rose stem cells (rose stem cell-derived exosomes) as an active ingredient.

As used herein, the term "rose (Rosa spp.)" refers to plants belonging to the genus Rosa, in the family Rosaceae, the order Rosales and the class Dicotyledoneae, and includes all of wild species and cultivated garden species.

As used herein, the term "exosomes" refers to nano-sized vesicles secreted or released from plant cells into extracellular spaces and having a membrane structure, and is also referred to as exosome-like vesicles or exosome-like particles.

As used herein, the term "skin elasticity" refers to a feature in which skin deformed by an external force easily returns to its original shape when the external force is removed. The term "skin wrinkles" refers to fine lines caused by skin aging. Skin wrinkles may be caused by genetic factors, reduction in collagen and elastin present in the skin dermis, external environmental factors, or the like. Accordingly, the term "skin wrinkle reduction or improvement" as used herein refers to suppressing or inhibiting the formation of wrinkles on the skin, or reducing already formed wrinkles.

In the cosmetic composition according to one embodiment of the present invention, the rose stem cells may be obtained by inducing a callus derived from rose embryos or leaves and then culturing cells of the callus.

The cosmetic composition according to one embodiment of the present invention may be, for example, cream or lotion.

Meanwhile, the cosmetic composition according to one embodiment of the present invention may suitably contain components which are generally used in cosmetic products, for example, moisturizers, antioxidants, oily components, UV absorbers, emulsifiers, surfactants, thickeners, alcohols, powder components, colorants, aqueous components, water, and various skin nutrients, etc., as needed, within the range that does not impair the effect of the present invention.

Furthermore, the cosmetic composition according to one embodiment of the present invention may include, in addition to the rose stem cell-derived exosomes, an agent for improving skin condition and/or a moisturizer, which have been used in the prior art, within the range that does not impair the effects (e.g., wrinkle improvement, skin regeneration, skin elasticity improvement, skin beauty, etc.). For example, the rose stem cell-derived exosomes of the present invention may be contained in or mixed with at least one of hydrogel, hyaluronic acid, salt of hyaluronic acid (e.g., sodium hyaluronate, etc.), or hyaluronate gel. In the cosmetic composition according to one embodiment of the present invention, the kind of hydrogel is not particularly limited, but the hydrogel may be preferably obtained by dispersing a gelled polymer in a polyhydric alcohol. The gelled polymer may be at least one selected from the group consisting of pluronic, purified agar, agarose, gellan gum, alginic acid, carrageenan, cassia gum, xanthan gum, galactomannan, glucomannan, pectin, cellulose, guar gum, and locust bean gum, and the polyhydric alcohol may be at least one selected from the group consisting of ethylene glycol, propylene glycol, 1,3-butylene glycol, isobutylene glycol, dipropylene glycol, sorbitol, xylitol, and glycerin.

The cosmetic composition according to one embodiment of the present invention may be used in various forms, for example, patches, mask packs, mask sheets, creams, tonics, ointments, suspensions, emulsions, pastes, lotions, gels, oils, packs, sprays, aerosols, mists, foundations, powders, and oilpapers. For example, the cosmetic composition may be applied to or soaked in at least one surface of a patch, a mask pack or a mask sheet.

The cosmetic composition is used for the purpose of skin regeneration, skin elasticity improvement, wrinkle improvement and the like, and the cosmetic composition may be prepared as any formulation which is generally prepared in the art. For example, it may be formulated as patch, mask pack, mask sheet, skin softener, nutrition, astringent lotion, nourishing cream, massage cream, eye cream, cleansing cream, essence, eye essence, cleansing lotion, cleansing foam, cleansing water, sunscreen, lipstick, soap, shampoo, surfactant-containing cleanser, bath preparation, body lotion, body cream, body oil, body essence, body cleanser, hairdye, hair tonic, etc., but is not limited thereto.

The cosmetic composition according to one embodiment of the present invention contains components which are commonly used in cosmetic products. For example, the cosmetic composition may contain conventional adjuvants and carriers, such as antioxidants, stabilizers, solubilizers, vitamins, pigments, and fragrances. In addition, other components in each formulation for the cosmetic composition may be suitably selected without difficulty by those skilled in the art depending on the type or intended use of the cosmetic composition.

Another embodiment of the present invention provides a cosmetic method for regulating mammalian skin conditions, except for treatment purposes, using the cosmetic composition. In the cosmetic method of the present invention, the expression "regulating skin conditions" means improving skin conditions and/or prophylactically regulating skin conditions, and the expression "improving skin conditions" means a visually and/or tactilely perceivable positive change in the appearance and feeling of skin tissue. For example, the expression "improving skin conditions" may include skin regeneration, skin elasticity improvement, and/or skin wrinkle reduction.

The cosmetic method according to one embodiment of the present invention includes: (a) applying the cosmetic composition directly to a mammalian skin; or (b) contacting or attaching a patch, a mask pack or a mask sheet, which has the cosmetic composition applied thereto or soaked therein, to the mammalian skin; or sequentially performing (a) and (b). In step (a), the cosmetic composition may be lotion or cream.

Alternatively, the cosmetic method according to one embodiment of the present invention may further comprise (c) removing the patch, mask pack or mask sheet from the mammalian skin after step (b), and applying the cosmetic composition to the mammalian skin. In step (c), the cosmetic composition may be lotion or cream.

In the cosmetic method according to one embodiment of the present invention, the mammal may be humans, dogs, cats, rodents, horses, cattle, monkeys, or pigs.

Advantageous Effects

The cosmetic composition for skin regeneration, skin elasticity improvement or skin wrinkle reduction containing rose stem cell-derived exosomes as an active ingredient according to the present invention has advantages that it is less likely to contain impurities such as growth regulators than conventional rose filtrates, rose extracts and conditioned media of rose callus, and is less cytotoxic than filtrates of conditioned media of rose stem cells (rose callus). In addition, the cosmetic composition of the present invention has excellent effects on skin regeneration, skin elasticity improvement and/or skin wrinkle reduction.

It should be understood that the scope of the present invention is not limited to the aforementioned effects.

BRIEF DESCRIPTION OF DRAWINGS

The patent or application file contains at least one drawing executed in color. Copies of this patent or patent application publication with color drawing(s) will be provided by the Office upon request and payment of the necessary fee.

EXAMPLES

Hereinafter, the present invention will be described in more detail with reference to the following examples. However, the following examples are only to illustrate the present invention and are not intended to limit or restrict the scope of the present invention. Those that can be easily inferred by those skilled in the art from the detailed description and examples of the present invention are interpreted as falling within the scope of the present invention. References referred to in the present invention are incorporated herein by reference.

Throughout the present specification, it is to be understood that, when any part is referred to as "comprising" any component, it does not exclude other components, but may further include other components, unless otherwise specified.

Example 1: Preparation of Rose Stem Cells

According to preparation and culture methods of plant stem cells known in the art, calluses were induced from rose embryos and/or leaves, and cells of the induced callus were cultured. In addition, a callus having a good growth state was selected and cultured in large amounts, thereby preparing conditioned media of rose stem cells.

Example 2: Preparation of Rose Stem Cell-Derived Exosomes

Figure 1A:
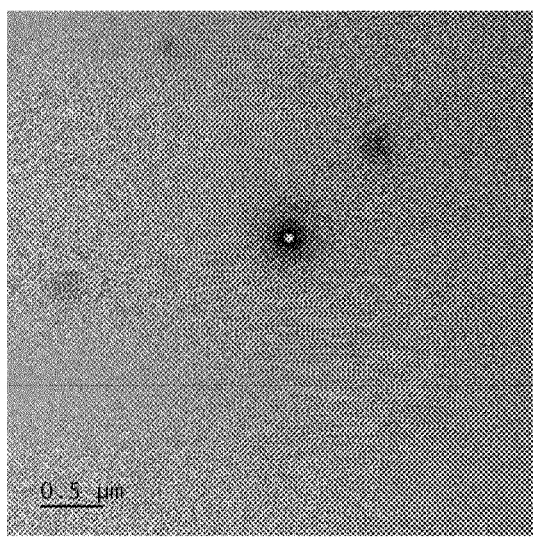
FIG. 1A shows particle images obtained by transmitted electron microscopy (TEM) of rose stem cell-derived exosomes obtained according to one embodiment of the present invention.
Figure 1A:
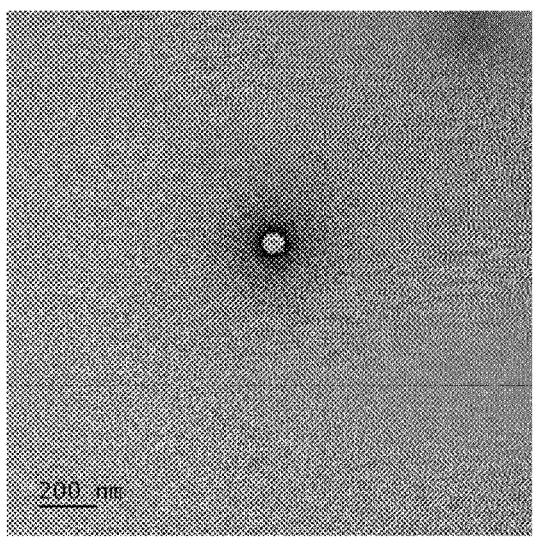
Figure 1A:
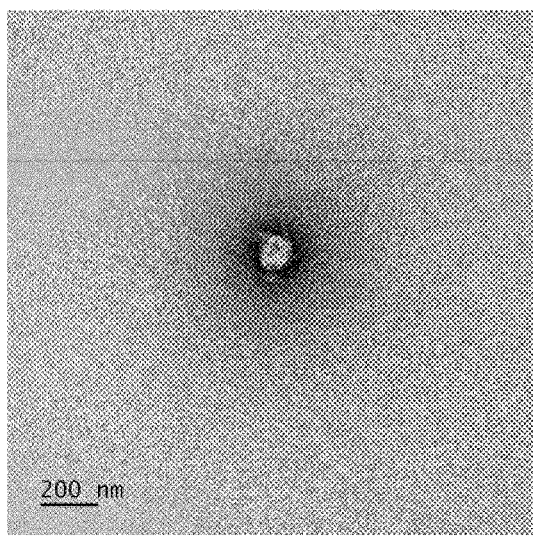
Figure 1A:
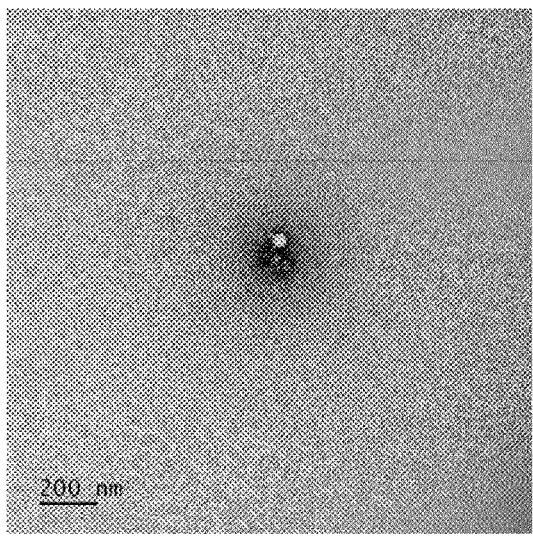
Figure 1B:
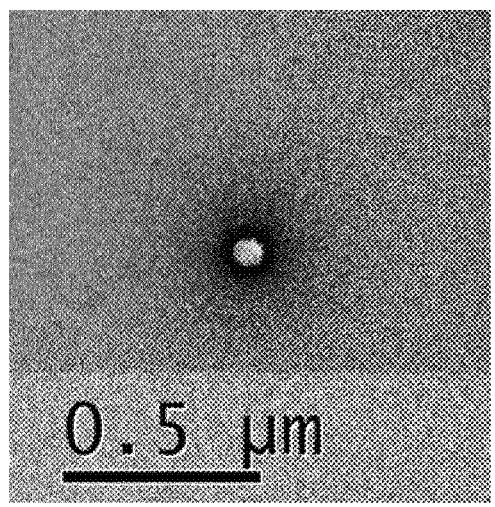
FIG. 1B shows enlarged particle images of FIG. 1A.
Figure 1B:
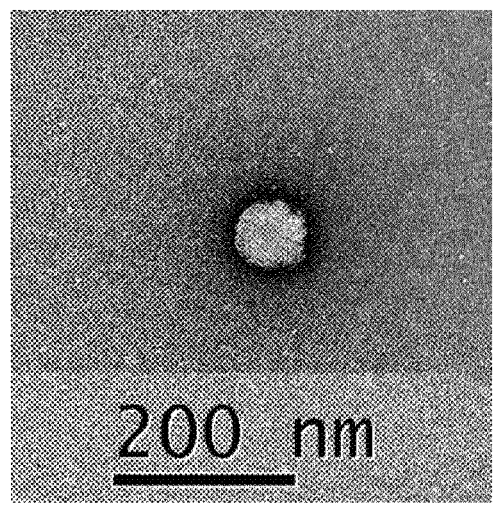
Figure 1B:
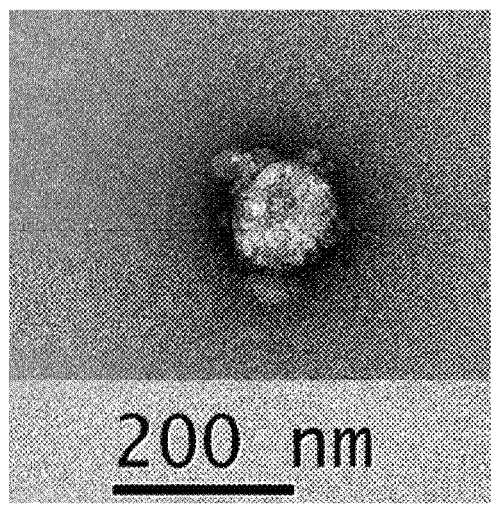
Figure 1B:
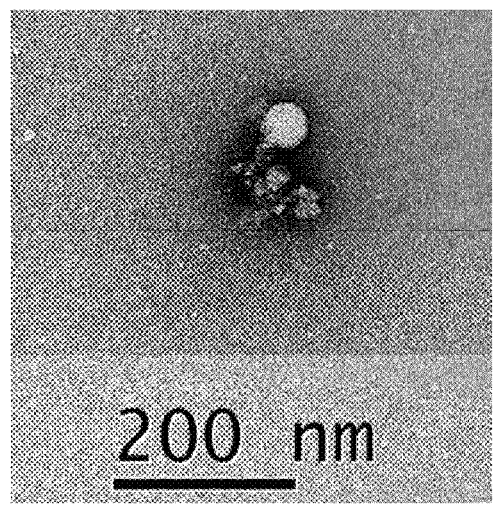
Figure 2:
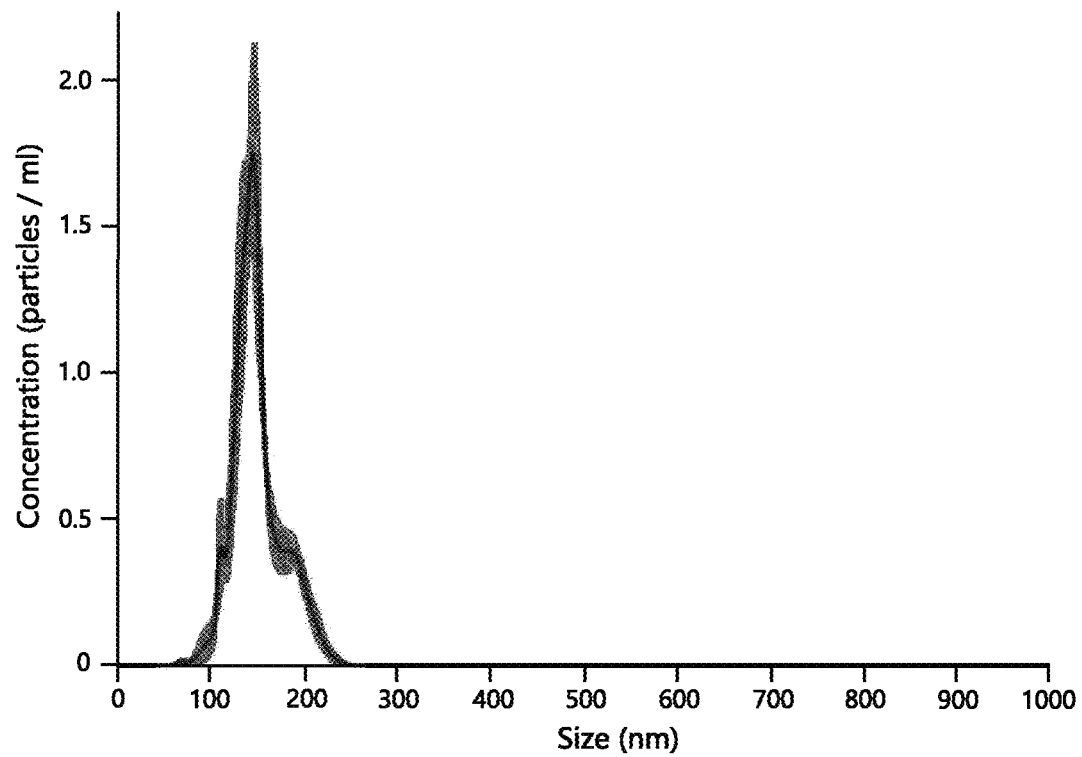
FIG. 2 is a graph showing the results of NTA analysis of rose stem cell-derived exosomes.

The conditioned media of rose stem cells prepared as described in Example 1 were purchased from BIO-FD&C Co., Ltd. (located in Incheon, Korea and supplying conditioned media of Damask Rose stem cells). The conditioned media of rose stem cells were filtered through a 0.22 μm filter to remove impurities such as cell debris, waste products and large particles. Rose stem cell-derived exosomes were isolated from the filtered conditioned media by tangential flow filtration (TFF) method. The size of the isolated rose stem cell-derived exosomes was analyzed by transmitted electron microscopy (TEM). As shown in FIGS. 1A and 1B, it was confirmed that the isolated rose stem cell-derived exosomes were nano-sized vesicles. The size and concentration of the rose stem cell-derived exosomes were analyzed by nanoparticle tracking analysis (NTA) using NS300 (purchased from Malvern Panalytical) (FIG. 2).

Figure 3:
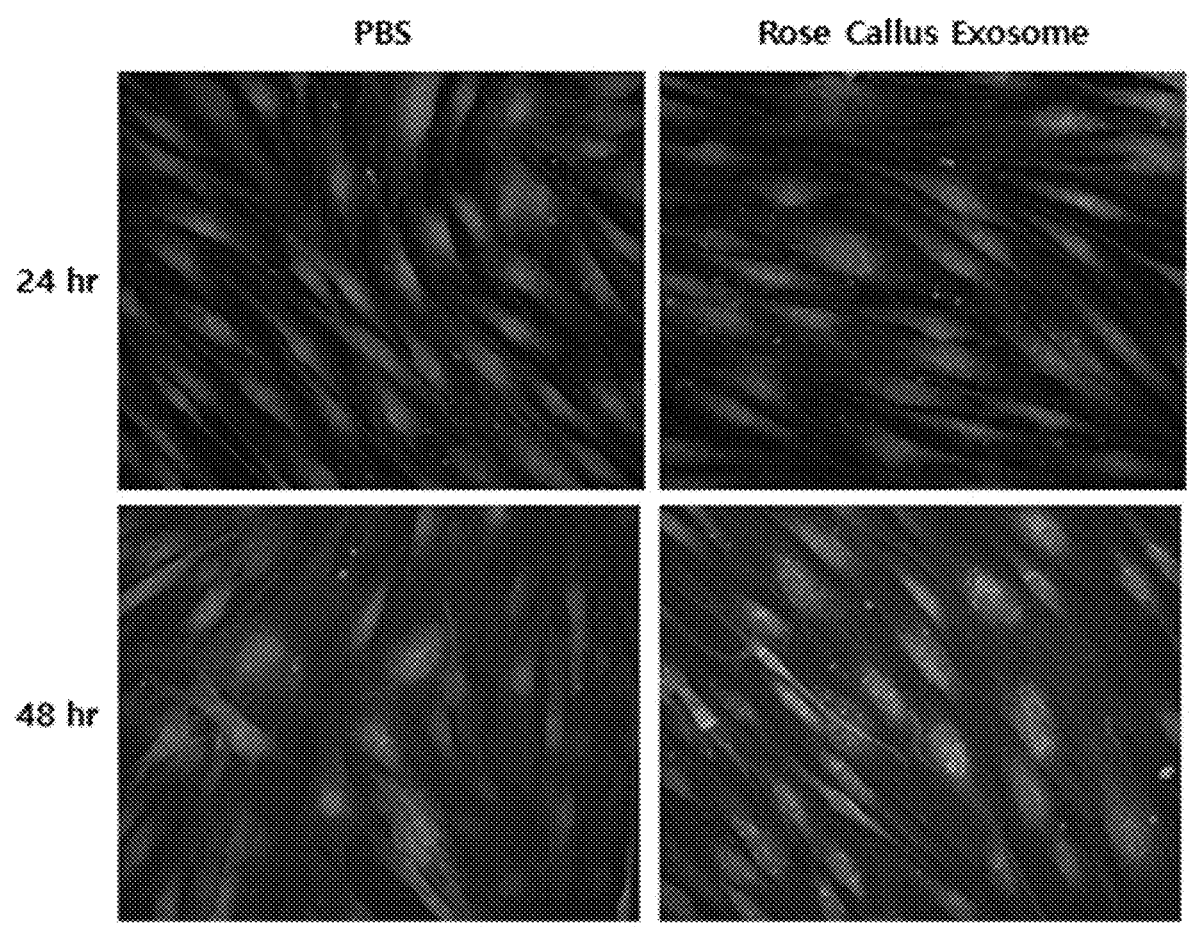
FIG. 3 depicts fluorescence microscopic images of cells showing that fluorescence-stained exosomes are delivered into human dermal fibroblasts (green: exosomes delivered into cells; blue: cell nucleus; and red: cell membrane).

Example 3: Evaluation of Delivery Ability of Rose Stem Cell-Derived Exosomes into Dermal Fibroblasts In order to examine whether the rose stem cell-derived exosomes would be delivered into human dermal fibroblasts (purchased from CEFO Co., Ltd., Seoul, Korea), the following analysis was performed. To fluorescence-stain the membrane of the rose stem cell-derived exosomes prepared in Example 2, the exosomes were allowed to react with PKH67 fluorescence dye (purchased from Sigma-Aldrich). After the reaction, the reaction solution was fractionated with an MW3000 column (purchased from ThermoFisher Scientific) to remove free PHK67 that was not stained in the exosome membrane. A negative control was prepared by allowing PKH67 fluorescence dye to react with a buffered solution and fractionating the reaction product with the MW3000 column. The exosomes stained with PKH67 were incubated with pre-cultured human dermal fibroblasts, and then whether the exosomes would be delivered into the cells over time was observed using a fluorescence microscope. Hoechst fluorescence dye (purchased from Sigma-Aldrich) was used to stain the cell nucleus, and CellMask Orange Plasma Membrane Stain fluorescence dye (purchased from ThermoFisher Scientific) was used to stain the cell membrane. As a result of examining whether the exosomes would be delivered into the cells, it was confirmed that the fluorescence-stained exosomes were delivered into the cells and green fluorescence accumulated in the cells over time (FIG. 3).

Example 4: Evaluation of Effect of Stimulating Collagen Production

Figure 4:
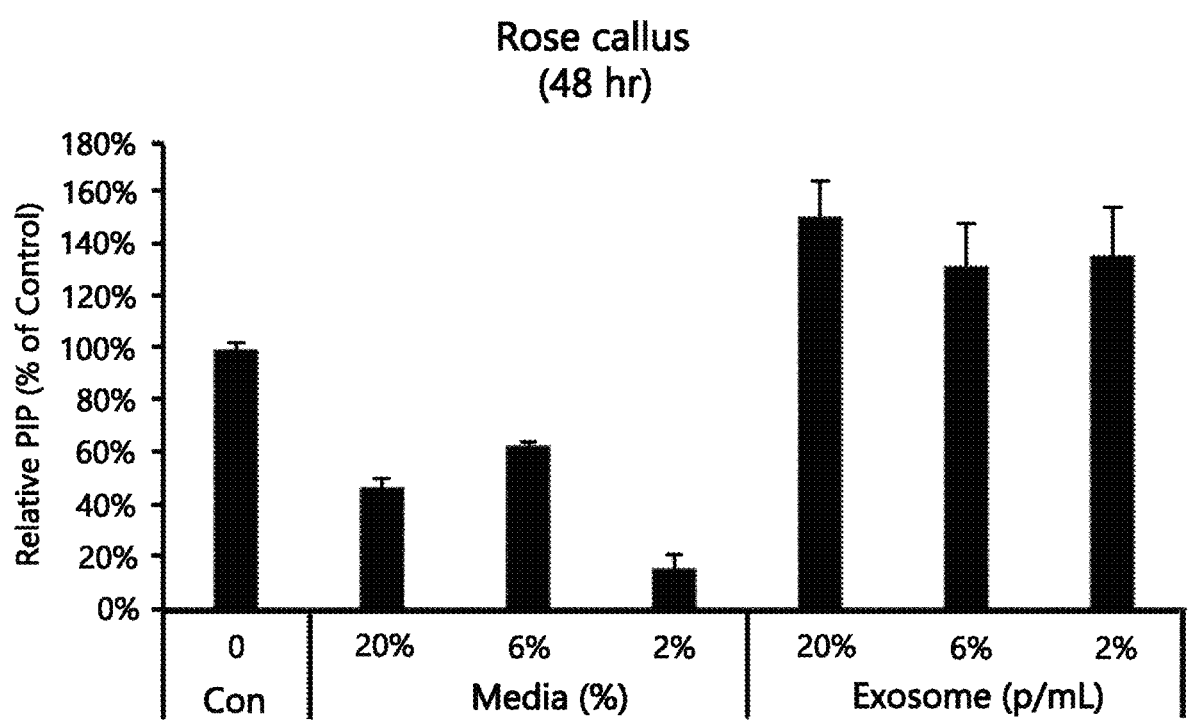
FIG. 4 is a graph showing the relative amount of collagen increases after human dermal fibroblasts are treated with rose stem cell-derived exosomes.

Human dermal fibroblasts (purchased from CEFO Co., Ltd.) dispersed in DMEM medium containing fetal bovine serum were dispensed into a multiwell plate, and then cultured for 24 hours and additionally cultured for 48 hours in serum-free medium. Thereafter, the conditioned media of rose stem cells or rose stem cell-derived exosomes prepared in Example 2 were diluted in serum-free medium to concentrations of 20%, 6% and 2%, and then the human dermal fibroblasts were treated with each of the dilutions and cultured. The concentrations of the rose stem cell-derived exosomes treated to the human dermal fibroblasts were $1.0 \times 10^9$ particles/mL (20%), $3.0 \times 10^8$ particles/mL (6%), and $1.0 \times 10^8$ particles/mL (2%), respectively. Next, the culture media were collected and centrifuged, and then the centrifuged media were prepared. The amount of collagen, which was synthesized from the human dermal fibroblasts and accumulated in the culture media, was measured using an Anti-Human Procollagen Type I C-peptide (PIP) EIA kit (purchased from Takara Bio) for procollagen type I C-peptide (PIP). The total protein amount of the cell lysate was measured with a BCA Protein Assay Kit (purchased from ThermoFisher Scientific). The amount of collagen was normalized by the total protein amount and the relative amount of collagen was calculated. As a result of measuring the amount of collagen, it was confirmed that the rose stem cell-derived exosomes of the present invention increased collagen synthesis in the human dermal fibroblasts (FIG. 4). However, the filtered conditioned media decreased collagen synthesis, as compared with the negative control (FIG. 4).

As can be seen from the above results, the cosmetic composition for skin regeneration, skin elasticity improvement or skin wrinkle reduction containing rose stem cell-derived exosomes as an active ingredient according to the present invention has a useful functional activity (i.e., an activity of increasing collagen synthesis) as a functional cosmetic. Thus, the rose stem cell-derived exosomes of the present invention are useful as an active ingredient of a cosmetic composition for skin regeneration, skin elasticity improvement or skin wrinkle reduction.

Example 5: Evaluation of Effect on Cell Viability

Human hair follicle dermal papilla cells (HDP cells; purchased from CEFO Co., Ltd.) were cultured in HDP culture medium (purchased from CEFO Co., Ltd.). HDP cells were seeded at a density of $1.5 \times 10^4$ cells per well, and then cultured at 37° C. under 5% $CO_2$ for 24 hours. The conditioned media of rose stem cells or the rose stem cell-derived exosomes were diluted in HDP culture medium to concentrations of 2%, 6% and 20%. The concentrations of the rose stem cell-derived exosomes treated to the HDP cells were $1.0 \times 10^8$ particles/mL (2%), $3.0 \times 10^8$ particles/mL (6%), and $1.0 \times 10^9$ particles/mL (20%), respectively.

Figure 5:
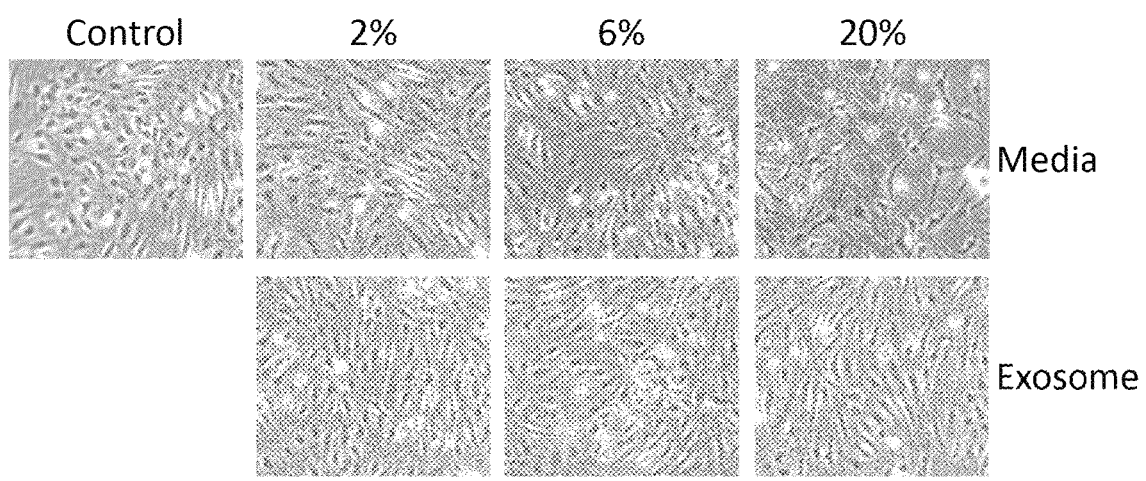
FIG. 5 shows optical micrographs obtained after treating human hair follicle dermal papilla cells with conditioned media of rose stem cells or rose stem cell-derived exosomes and then culturing the treated cells for 48 hours. From FIG. 5, it can be seen that, when human hair follicle dermal papilla cells were treated with 20% of conditioned media of rose stem cells, almost all the human hair follicle dermal papilla cells lost their original shape and were in a dead state.

The HDP cells were treated with the conditioned media of rose stem cells or the rose stem cell-derived exosomes and cultured, and then the state of the cells was observed with an optical microscope. As shown in FIG. 5, it was confirmed that, in the experimental groups treated with high concentrations (6% and 20%) of the conditioned media of rose stem cells, a significant number of the HDP cells lost their original shape and were in a dead state. However, it was confirmed that, when the HDP cells were treated with the rose stem cell-derived exosomes of the present invention, almost all the HDP cells did not die and were in a normal state.

Figure 6:
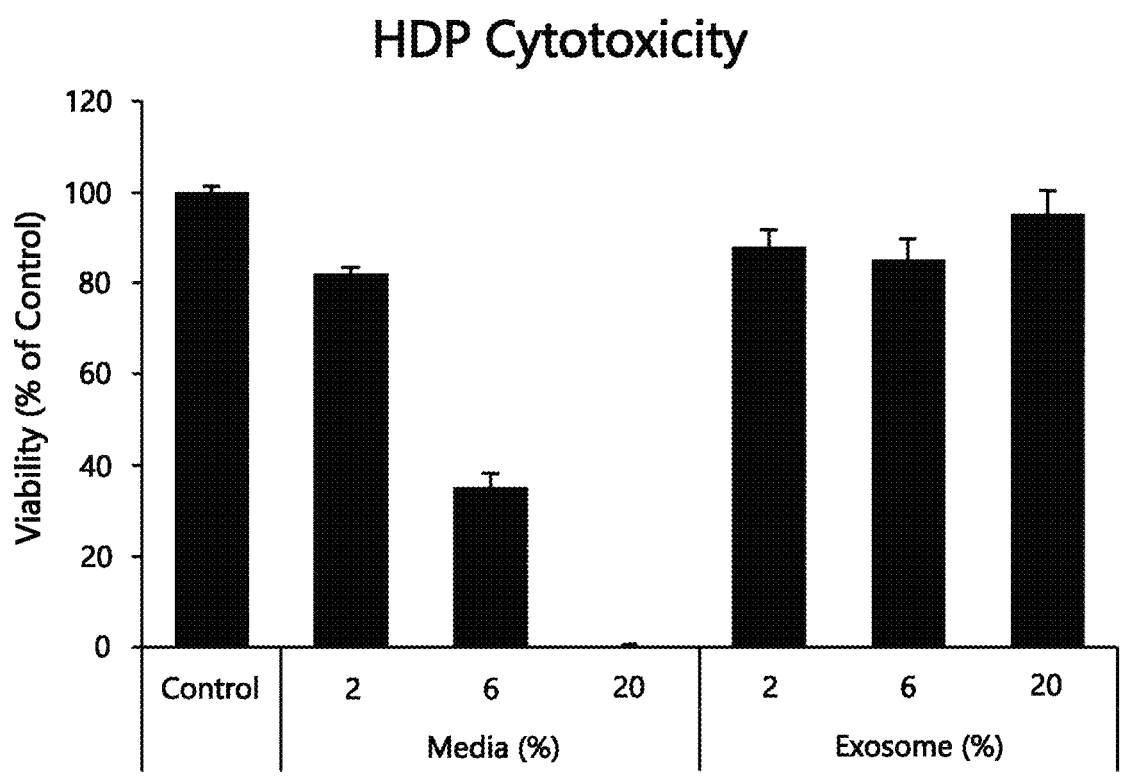
FIG. 6 shows the viability of human hair follicle dermal papilla cells, which were treated with conditioned media of rose stem cells and then cultured for 48 hours, and the viability of human dermal hair follicle papilla cells which were treated with rose stem cell-derived exosomes and then cultured for 48 hours. The viabilities are expressed as percentages relative to a negative control group (an experimental group treated only with culture medium.

In addition, in order to quantitatively evaluate the above observation results, HDP cells were cultured for 48 hours in media supplemented by the conditioned media of rose stem cell or the rose stem cell-derived exosomes, and then the viability of the cells was measured using a CCK-8 assay kit (purchased from Dojindo). As a result of measuring the cell viability, it was confirmed that, when the cells were treated with the conditioned media of rose stem cell, the cell viability decreased in a concentration-dependent manner, whereas, when the cells were treated with the rose stem cell-derived exosomes of the present invention, there was no substantial change in the cell viability, indicating that the rose stem cell-derived exosomes have little effect on the cell viability, that is, have low cytotoxicity (FIG. 6).

Although the present invention has been described with reference to the embodiments, the scope of the present invention is not limited to these embodiments. Any person skilled in the art will appreciate that various modifications and changes are possible without departing from the spirit and scope of the present invention and these modifications and changes also fall within the scope of the present invention.

We claim:

1. A method for skin regeneration, skin elasticity improvement or skin wrinkle reduction in a subject in need thereof, the method comprising
    treating a skin of the subject with a composition comprising isolated exosomes derived from rose stem cells as an active ingredient, wherein the exosomes are isolated from a conditioned medium of the rose stem cells,
    wherein the treating the skin with the composition promotes collagen production but reducing cytotoxicity in the skin.

2. The method of claim 1, wherein the rose stem cells are obtained by inducing a callus from rose embryos or leaves and then culturing cells of the callus.

3. The method of claim 1, wherein the composition is used in at least one form selected from the group consisting of a patch, a mask pack, a mask sheet, a cream, a tonic, an ointment, a suspension, an emulsion, a paste, a lotion, a gel, an oil, a pack, a spray, an aerosol, a mist, a foundation, a powder, and an oilpaper.

4. The method of claim 3, wherein the composition is applied to or soaked in at least one surface of the patch, the mask pack, or the mask sheet.

5. The method of claim 1, wherein the composition is a skin external preparation or a cosmetic composition.

6. The method of claim 1, wherein the composition is a cream or a lotion.

7. The method of claim 1, wherein the subject is at least one selected from the group consisting of a human, a dog, a cat, a rodent, a horse, a cattle, a monkey, and a pig.

8. A method for skin regeneration, skin elasticity improvement or skin wrinkle reduction in a subject in need thereof, the method comprising steps of:
    (a) (a1) applying a composition comprising isolated exosomes derived from rose stem cells as an active ingredient to a skin of the subject in need thereof, wherein the exosomes are isolated from a conditioned medium of the rose stem cells; or (a2) contacting or attaching a patch, a mask pack or a mask sheet, which has the composition applied thereto or soaked therein, to the skin; or (a3) sequentially performing (a1) and (a2); and
    (b) leaving the composition on the skin for a period of time sufficient to promote collagen production but reduce cytotoxicity in the skin.

9. The method of claim 8, wherein the rose stem cells are obtained by inducing a callus from rose embryos or leaves and then culturing cells of the callus.

10. The method of claim 8, wherein the composition is a lotion or a cream in step (a).

11. The method of claim 8, further comprising step (c) removing the patch, the mask pack, or the mask sheet from the skin after step (b), and applying the composition to the skin.

12. The method of claim 11, wherein the composition is a lotion or a cream in step (c).

13. The method of claim 8, wherein the composition is used in at least one form selected from the group consisting of a patch, a mask pack, a mask sheet, a cream, a tonic, an ointment, a suspension, an emulsion, a paste, a lotion, a gel, an oil, a pack, a spray, an aerosol, a mist, a foundation, a powder, and an oilpaper.

14. The method of claim 13, wherein the composition is applied to or soaked in at least one surface of the patch, the mask pack, or the mask sheet.

15. The method of claim 8, wherein the composition is a skin external preparation or a cosmetic composition.

16. The method of claim 8, wherein the subject is at least one selected from the group consisting of a human, a dog, a cat, a rodent, a horse, a cattle, a monkey, and a pig.

* * * * *